United States Patent [19]

Fattinger et al.

[11] Patent Number: 5,712,705
[45] Date of Patent: Jan. 27, 1998

[54] ARRANGEMENT FOR ANALYSIS OF SUBSTANCES AT THE SURFACE OF AN OPTICAL SENSOR

[75] Inventors: Christof Fattinger, Blauen, Switzerland; Burkhard Danielzik, Ingelheim, Germany; Dieter Graefe, Jena, Germany; Martin Heming, Saulheim, Germany; Frank-Thomas Lentes, Bingen, Germany

[73] Assignees: Carl Zeiss Jena GmbH, Jena, Germany; F. Hoffman-La Roche, Basel, Switzerland; Schott Glaswerke, Mainz, Germany

[21] Appl. No.: 481,376

[22] PCT Filed: Nov. 14, 1994

[86] PCT No.: PCT/EP94/03769

§ 371 Date: Jul. 7, 1995

§ 102(e) Date: Jul. 7, 1995

[87] PCT Pub. No.: WO95/14225

PCT Pub. Date: May 26, 1995

[30] Foreign Application Priority Data

Nov. 15, 1993 [DE] Germany .................. 43 38 894.9
Sep. 22, 1994 [DE] Germany .................. 44 33 753.1

[51] Int. Cl.$^6$ ........................................ G01B 9/02
[52] U.S. Cl. .............................. 356/354; 356/359
[58] Field of Search ........................ 356/345, 354, 356/359, 360, 351, 349

[56] References Cited

U.S. PATENT DOCUMENTS

| | | |
|---|---|---|
| 5,082,629 | 1/1992 | Burgess et al. . |
| 5,392,121 | 2/1995 | Hosaka et al. ............. 356/351 |

FOREIGN PATENT DOCUMENTS

| | | |
|---|---|---|
| 0 226 604 | 5/1986 | European Pat. Off. . |
| 89108567 | 5/1989 | European Pat. Off. . |
| 0 455 067 | 4/1991 | European Pat. Off. . |
| 0 482 377 | 4/1992 | European Pat. Off. . |
| 94103973 | 3/1994 | Switzerland . |
| WO89/07756 | 8/1989 | WIPO . |
| WO 93/01487 | 1/1993 | WIPO . |
| WO93/01487 | 1/1993 | WIPO . |

OTHER PUBLICATIONS

K. Tiefenthaler et al. "Integrated optical switches and gas sensors", Optics Letters vol. 10, No. 4, Apr. 1984, pp. 137–140.

T. Suhara et al, IEEE, J. Quantum Electron. vol. QE–22, No. 6, Jun. 1986, pp. 845–867.

K. Tiefenthaler et al. "Sensitivity of grating couplers as integated-optical chemical sensors", J. Opt. Soc. Am. B, vol. 6, No. 2, Feb. 1989, pp. 209–220.

W. Lukosz et al, "Output Grating Couplers on Planar Waveguides as Integrated Optical Chemical Sensors", Sensors and Actuators B1, 1990, pp. 585–588.

(List continued on next page.)

*Primary Examiner*—Frank G. Font
*Assistant Examiner*—Robert Kim
*Attorney, Agent, or Firm*—McAulay Fisher Nissen Goldberg & Kiel, LLP

[57] ABSTRACT

Arrangement for analysis of substances at or near the surface of an optical sensor with at least one wave-guiding film and at least one multidiffraction grating coupler for in-coupling and out-coupling of light beams, in which at least two light beams enclosing an angle $\alpha$ relative to one another are coupled in and by which at least two light beams enclosing an angle $\phi$ relative to one another are coupled out, and with a detection system for detecting the out-coupled light beams, wherein in-coupling and out-coupling are effected on one and the same side of the sensor and the in-couple beams and out-couple beams lie in different quadrants of the plane of incident light, and the angle $\alpha$ between the in-couple beams is greater than the angle $\phi$ between the out-couple beams. The arrangement has multiple uses for determining physical or chemical measured quantities based on the interaction of the guided light waves with the medium at or near the sensor surface.

56 Claims, 11 Drawing Sheets

OTHER PUBLICATIONS

D.S. Goldman et al, "Miniaturized spectrometer employing planar waveguides and grating couplers for chemical analysis", Applied Optics, vol. 29, No. 31, Nov. 1990, pp. 4583–4589.

W. Lukosz, "Principles and sensitivities of integrated optical and surface plasmon sensors for direct affinity sensing and immunosensing", Biosensors & Bioelectronics 6, 1991, pp. 215–225.

D. Clerc et al, "Integrated optical output grating coupler as refractometer and (bio–)chemical sensor", Sensors and Actuators B11, 1993, pp. 461–465.

Ch. Fattinger, "The bidiffracte grating coupler", Appl. Phys. Lett. 62 (13), Mar. 1993 pp. 1460–1462.

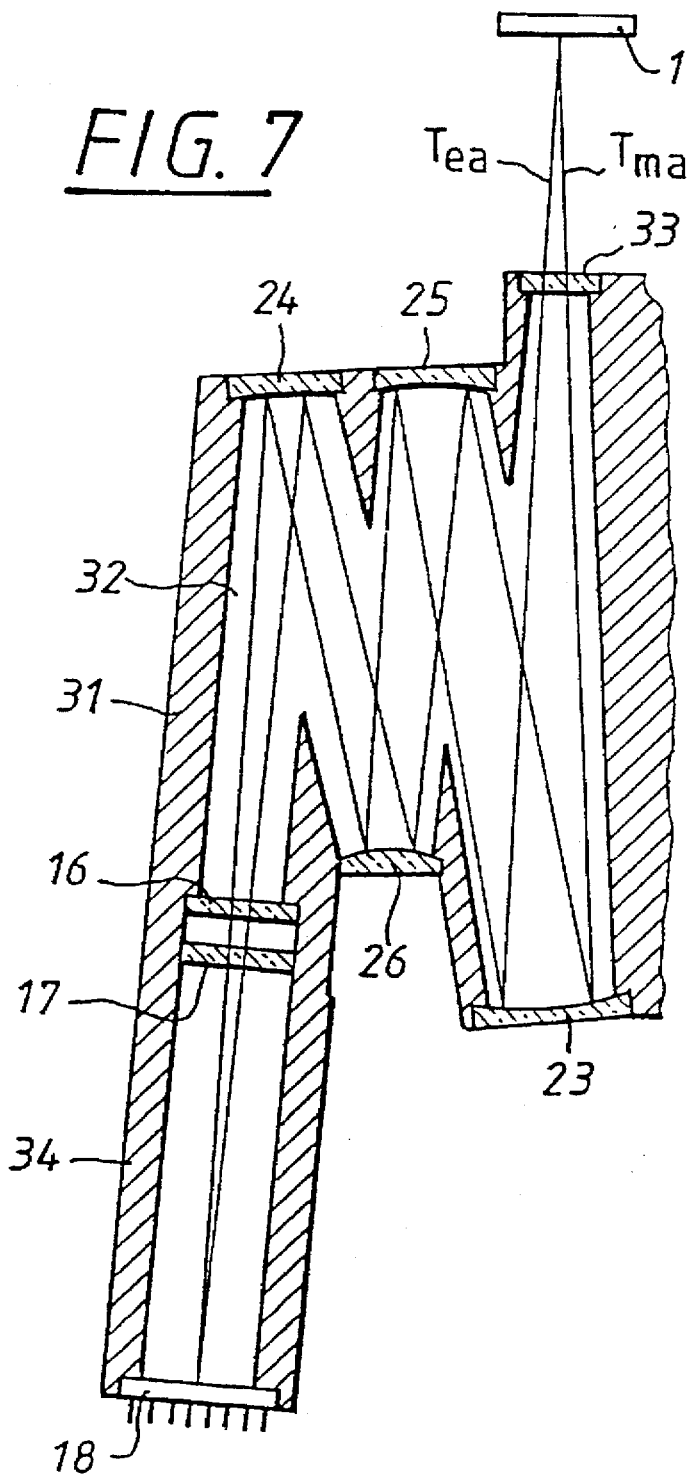
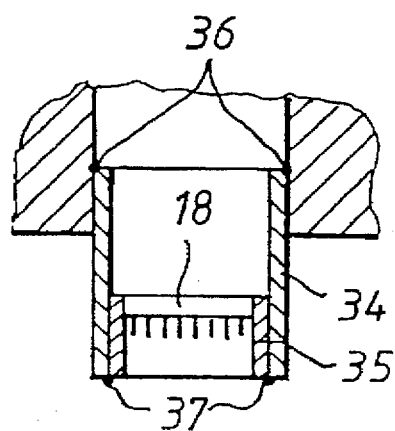

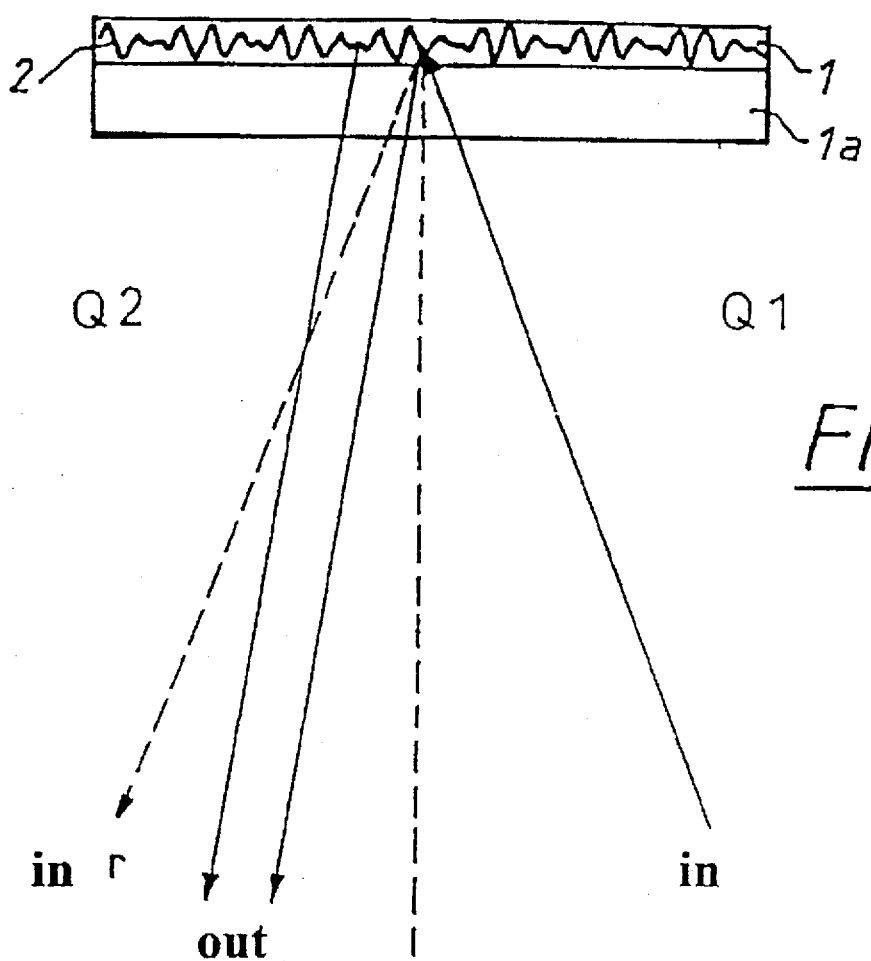

ID=arrangement-for-analysis-of-substances-at-the-surface-of-an-optical-sensor>
ARRANGEMENT FOR ANALYSIS OF SUBSTANCES AT THE SURFACE OF AN OPTICAL SENSOR

BACKGROUND OF THE INVENTION a) Field of the Invention

The invention is directed to an arrangement for analysis of substances at or near the surface of an optical sensor with at least one wave-guiding film and at least one multidiffraction grating coupler for in-coupling and out-coupling of light beams.

b) Description of the Related Art

Arrangements of this type are used, according to the prior art, for analyzing substances near the sensor surface. They are used in multiple applications for determining physical or chemical measured quantities [references 3–5, 10–11]. Operation of the sensors is based upon the interaction of guided light waves with the medium at and near the sensor surface. On this basis, such sensors can be used in combination with an arrangement for operation as universal spectrometers, since the index of refraction and the absorption of the medium in the vicinity of the sensor surface can be determined. Applications for affinity sensing [see reference 5] are also known. In this case, the molecules to be determined bond selectively at the sensor surface and are determined through their interaction with the guided wave.

The use of one or more grating couplers for in-coupling and/or out-coupling of the guided wave is known in the art [see reference 1,2].

The use of a grating coupler for in-coupling is known from [see reference 8]. The guided waves occurring when resonance is achieved are determined by detecting the light exiting laterally from the waveguide. This method imposes strict requirements on the planarity of the waveguide and on the accuracy of angular adjustment, which represents a drawback for economical application.

The implementation of this method described in [reference 6] with determination of the autocollimation angle also requires a very precise mechanical angular adjustment.

Angular adjustment may be dispensed with if a grating is used for out-coupling and the exiting radiation is guided to one or two position-sensitive detectors as described in [reference 7]. However, this method requires that the guided waves be coupled in via the end face of the waveguide. This is disadvantageous due to the required preparation of the end faces and accuracy of positioning of the sensor when coupling in. The implementation of this method which is described in [reference 14] also has these disadvantages. Further, the method according to [reference 14] requires that two light sources be coupled in from different directions. This further increases the cost of the end face coupling. Moreover, the effect of temperature changes on the detection of measurement values is disadvantageous if the guided waves pass through the sensor in different directions.

A spectrometer based on optical waveguides with grating couplers is described in [references 9, 13]. In this process, changes in the absorption characteristics at the waveguide surface are determined for different wavelengths.

A known advantageous construction of a grating coupler is the multidiffraction coupler [reference 11], especially the bidiffraction coupler [see reference 15]. The out-coupled waves can be detected without background with a method of this kind.

It is already known [reference 7] to determine chemical substances by bringing the probe containing the substance to be determined into contact with the wave-guiding film of an optical film waveguide, to couple coherent light into the wave-guiding film and guide it therein as a light wave and to couple the light out of the latter again, wherein a diffraction grating is provided in the plane of the wave-guiding film for in and out coupling of light. Two coherent (e.g., orthogonally polarized) light beams can be coupled into the film waveguide simultaneously and, by interference of two out-coupled partial beams produced by the two (e.g., orthogonally polarized) light waves which are guided conjointly in the waveguide, the relative phase position can be measured in the form of a phase difference of the two in-coupled light fields or the relative intensity of the out-coupled light fields can be determined [see reference 11].

A coherent light field can be coupled into and out of a waveguide in a simple manner by grating couplers without relying on a focussing optical system. The light field is coupled in when it strikes the region of the waveguide provided with the grating coupler at a determined angle of incidence which depends on the grating period and the effective mode refractive index. When a so-called multidiffraction grating structure is used for in-coupling and out-coupling, the diffraction angle and the intensities of the individual orders of diffraction can be varied independently from one another. The out-coupled partial beam guided in the waveguide can be separated from reflected, transmitted or directly diffracted partial beams, although the regions on the wave-guiding film in which the light fields are coupled in and coupled out partially overlap.

Possible embodiment forms of the sensor are described in [references 11, 16]. Two light fields are to be coupled into the sensor with different or identical polarization, depending on the construction.

A process in which a grating integrated in the sensor serves for in-coupling as well as out-coupling is described in [reference 12]. Fanned illumination is required for in-coupling and a mechanical diaphragm is required in the out-couple beam path to suppress reflected light. The disadvantage in this method consists in the required positioning accuracy with respect to the diaphragm, the sharp divergence of the in-coupling and out-coupling directions from the surface normal, and the widely differing diffraction intensity in the different orders of the guided waves. The use of a plane mirror system arranged downstream of the lens and in front of the detector for reducing overall length is also described in [reference 12].

OBJECT AND SUMMARY OF THE INVENTION

The primary object of the present invention is to achieve an angular separation of the in-coupled and out-coupled beams and a separation of the out-coupled beams from the beams reflected at the sensor.

This object is met by an arrangement for analysis of substances at or near the surface of an optical sensor with at least one wave-guiding film and at least two light beams enclosing an angle α relative to one another are coupled in and by which at least two light beams are enclosing an angle φ relative to one another are coupled out, and with a detection system for detecting the out-coupled light beams, wherein in-coupling and out-coupling are effected on one and the same side of the sensor and the in-couple beams and out-couple beams lie in different quadrants of the plane of incident light, and the angle α between the in-couple beams is greater than the angle φ between the out-couple beams. The invention is directed to an arrangement for analysis of substances by measurement of light absorption at or near the surface of an optical sensor comprising at least one waveguiding film and at least one multidiffraction grating coupler for in-coupling and out-coupling of light beams; wherein at least one light beam is coupled in and at least one light beam is coupled out, and with a detection system for detecting the out-coupled light beams; and wherein in-coupling and out-coupling are effected on one and the same side of the sensor, the in-couple beams and out-couple beams lie in different quadrants of the plane of incident light, and the in-couple beam is adjustable with respect to the in-coupling angle and is also slightly convergent.

Still further, the invention is directed to an arrangement for analysis of substances at or near the surface of an optical sensor comprising at least one wave-guiding film and at least one multidiffraction grating coupler for in-coupling and out-coupling of light beams; wherein at least two light beams enclosing an angle α relative to one another are coupled in; and wherein the light from a light source reaches at least one beam splitter which splits it into at least two partial beams and the partial beams are guided into the sensor surface via beam-deflecting optics and beam offsetting units and at least one imaging unit.

The invention is also directed to an arrangement for imaging the interference pattern of the radiation components coupled out of a waveguide via a multidiffraction grating, formed of a combination of folded beam path and imaging mirrors which is arranged downstream of the exit location and images the interference pattern on a position-resolving receiver via a polarizer.

The out-coupled beams are angularly separated after long beam paths and are easily analyzable. Long beam paths are produced, for example, by folding.

Surprisingly, the angle configuration according to the invention proves to be particularly insensitive to slight tilting of the sensor about the horizontal plane, especially in the case of slight differences in the angles of the out-coupled beams. This is of great importance, above all, when exchanging sensors.

The angular displacement is noticeably facilitated by means of a slight beam convergence of the in-coupled beams.

A further advantage of the arrangement according to the invention consists in the compact construction of the beam guidance system in an integrated module in which all of the light beams required for using the sensor can be coupled in, coupled out and detected.

The miniaturization which is made possible in this way is also advantageous for reasons of stability relative to environmental influences (e.g., thermal effects, vibrations).

A semiconductor laser diode or superluminescent diode is preferably used as a light source, since it can be integrated directly in the readout head. For installation, mounting is effected in a particularly advantageous manner at the outer side of a housing containing the rest of the arrangement so that the semiconductor unit can be exchanged in the event of a defective light source without opening the housing. A construction in which the radiation diode is arranged together with the necessary units for stabilizing wavelength and output (e.g., reference diode, temperature stabilization) in a common housing is especially advantageous.

In this way, the temperature stabilization unit can be constructed with low thermal capacity enabling an economical construction of the necessary power supply electronics.

As an alternative to a laser diode or superluminescent diode, a different coherent light source can also be used, e.g., a He Ne laser. In order to retain the compact construction of the readout head regardless of the dimensions of the light source, the light is advantageously supplied to the readout head via a lightguide in this case. When using a light source with lightguide feed to the readout head, it is also possible to change the light source and wavelength more quickly when using a standard lightguide coupling.

Some of the optical elements needed for beam shaping can be integrated directly in the housing of the laser diode or superluminescent diode or, alternatively, in the plug-in connector for the lightguide. Further, additional elements for adapting to the beam parameters can be arranged within a housing containing the arrangement, e.g., behind the beam splitter. Astigmatic beam profiles, for instance, may also be realized by using cylindrical units with a different focal length vertically to and parallel to the plane of incidence.

The division into two independent light fields for coupling the guided wave into the sensor is effected by means of a beam splitter, e.g., in the form of a semitransparent mirror or a holographic element. The advantage of a holographic element consists in that mirror elements may be dispensed with in the subsequent beam guidance system. The beam guidance system is formed of a plurality of mirrors which guide the light for both in-coupling arms of the arrangement to the sensor. Alternatively, the beam splitting can be realized by a glass-fiber branching element.

The adjustment of the beam parameters of the two in-coupling arms in the sensor plane is effected by means of focussing optics. In so doing, a common optical system or two separate optical systems can be used for focussing the two light fields to be coupled in. Different beam parameters can be realized vertically and parallel to the plane of incidence by using cylindrical optics.

The in-coupling conditions for the two incident light fields are to be maintained for operating the optical waveguiding sensor. These conditions are determined by the effective mode refractive index of the guided waves and the utilized periods of the grating coupler.

Changes in the in-coupling angle are made necessary by the limited chip-to-chip reproducibility of the sensor and, further, by changes in the effective mode refractive indices due to substances in the vicinity of the sensor surface. The in-coupling angle can be adjusted by introducing a variable-position slit diaphragm in the respective in-couple beam path. By moving the diaphragm within the plane of incidence, an in-coupling angle can be selected from the angular range determined by the beam divergence. A filter with spatially variable transmission can be used as an alternative to a mechanically linearly moved slit diaphragm.

This diaphragm can be realized in a particularly advantageous manner by a liquid crystal element with rod-shaped image elements arranged in a linewise manner, where the line direction lies within the plane of incidence: the respective transmitting image elements define the in-coupling angle. This solution does not require any moving parts for angular adjustment. The adjustment of the coupling angle is to be carried out independently for the two in-couple beam paths. Two separate elements or a common element can be used for this purpose. When using a common element, variably controllable regions are to be provided for the two in-couple beam paths. The fact that only one holder is required is advantageous for miniaturization and a simple construction.

The LCD units are preferably positioned in the vicinity of the focussing element so that a departure of the beam profile in the sensor plane from a Gaussian distribution can be kept at a minimum. Further, to achieve a Gauss-like beam profile, it is advantageous with respect to the rod-shaped image elements of the liquid crystal unit to adjust more than two different transmission values. The secondary maxima in the sensor plane caused by the diffraction at the diaphragm can be reduced by a transmission characteristic which is graduated in this way.

Alternatively, simple mechanical adjusting units can also be used instead of the LCD units.

It is especially advantageous to use swivelable planeparallel glass parallelepipeds as beam offsetting units whose beam offset results in a change in the beam direction after passing through an imaging element.

An embodiment form which totally dispenses with the LCD elements or mechanical elements required for adjusting the in-coupling angle is advantageous for realizing the arrangement according to the invention in a simple and economical manner. For this simple construction it must be ensured by means of close tolerances of the sensor and limited changes in the effective mode refractive indices during operation of the sensor that possible changes in the in-coupling angle lie within the convergence angle of the incident light fields.

In optical wave-guiding sensors with one or more integrated optical diffraction gratings, the alignment of the grating lines defines the propagation direction of the guided waves. Accordingly, the plane of incidence and emergence plane for the in-coupled and out-coupled light fields are determined in conjunction with the selection of an in-coupling location.

It is particularly advantageous to couple light in and out on the side of the waveguide remote of the sensor surface since the substance to be analyzed can accordingly be brought to the sensor surface in a much simpler manner. The arrangement for operating the sensor can accordingly be separated in a simple manner from the device for advancing the substances.

It is particularly advantageous to guide the in-coupled and out-coupled radiation components in different quadrants of the in-coupling and out-coupling plane. In an embodiment form of the arrangement according to the invention, the out-coupled light fields are guided by an imaging system to a position-resolving receiver. The imaging is advantageous because slight changes in direction of the out-coupled light beams do not affect the measured quantities. One or more lenses or mirrors can be used for imaging. The construction with an imaging element is particularly simple.

With the use of two or more imaging elements, preferably as a double collimator arrangement, partial regions of the beam path can be realized with substantially parallel light; filter elements can be advantageously included therein.

The inventive combination of folding and imaging via imaging mirrors is particularly advantageous. The telescopic, preferably telecentric, construction of the imaging system is advantageous since a low sensitivity to changes in distance between the sensor and the arrangement can be achieved in this way. This imaging can be produced by spherical, aspheric or cylindrical mirrors or combinations thereof.

Different image scales can be selected vertically and parallel to the exit plane. The scale in the plane is adapted to the position resolution of the detector and the scale vertical to the exit plane is matched to the height of the image elements of the detector. Since changes in the image scale parallel to the exit plane reduce the accuracy of measurement detection, it is advantageous when selecting materials for the out-couple beam path to balance the thermal expansion of the individual components. An optimal temperature stability can be achieved for the image scale by means of this homologous expansion. The elements required for imaging can be constructed as mirrors, lenses, Fresnel lenses or holographic optical elements.

As was already suggested, analysis of the phase difference between the TE mode and TM mode of the waves guided in and coupled out of the sensor by means of a position-resolving detector requires the inclusion of a polarizing element, e.g., a polarizing filter, in the out-coupled beam path in order to cause interference between the two modes.

As an alternative to determination of phase difference, absorption measurements can also be carried out with the out-coupled light fields on the position-resolving detector. In this measuring method, measurement of the damping characteristics of the guided wave can provide information on substances near the sensor surface. In this case, the out-coupled light can be measured for one of the two modes of the guided wave. Only one mode is coupled in during measurement. However, relative measurements are also possible when coupling in and measuring both modes.

The phase difference between TE mode and TM mode can be measured in a particularly simple manner by focussing the out-coupled light beams on one or more position-sensitive detectors (PSD) instead of imaging on a position-resolving detector. In so doing, the TE mode or TM mode produces a focus in the detector plane in each instance. The distance between the two foci is measured.

The advantage of this measuring principle consists in that changes in direction of the out-coupled light beams brought about by slight tilting of the sensor have no effect on the measured quantity.

The arrangement according to the invention can be realized more simply and economically by using PSD's, since the cost of the detectors and required electronics is appreciably lower compared to the construction with the position-resolving detector. Only a reduced sensitivity compared to the position-resolving construction can be realized with this reduced expenditure.

When using an individual PSD, alternating in-coupling of the two light fields is required for measuring the phase difference between the TE mode and TM mode. One of the possible solutions described above for adjusting the in-coupling angle is required for this purpose, so that the in-coupling condition is met for only one of the two modes as selected. When using more than one PSD unit, it is possible to ensure, based on the dimensioning of the grating coupler, that the out-coupled light fields will lie on different PSD's. In this case, the distance between the center points of the two foci can be measured continuously for both modes so that there will be no time differences during measurement, e.g., as a result of switching in-coupling.

As was described above, the elements needed for focussing can be constructed as imaging mirrors, lenses, Fresnel lenses or holographic optical elements.

Different focal lengths for focussing parallel and vertically to the plane of incidence of the detector can be used in an expeditious manner to adjust an optimal diameter of the beam spot for the spatial resolution of the detector.

In contrast to the prior art, all of the embodiment forms of the arrangement according to the invention described above offer the advantage of substantially lower requirements with respect to temperature stability. The guided waves pass through the sensor in the same direction so that temperature drift can be compensated for to a good approximation by the differential measurement of the effective refractive indices of the modes. Further, the requirements for positioning and mechanical stability of the sensor are also appreciably lower compared to the grating couplers of the prior art, since there is no angular measurement of the out-coupled light beams relative to the waveguide plane. A further advantage consists in the insensitivity to slight tilting of the sensor relative to the arrangement according to the invention.

The compact construction is advantageous in that low sensitivity to changes in temperature and to vibrations is achieved in this way and the arrangement according to the invention can be integrated in the analytical systems as a module in a simple manner.

Moreover, particularly when a bidiffraction coupler is used, the arrangement according to the invention has the advantage that no end face in-coupling is required and a slight displacement of the sensor in the plane of the waveguide has no effect on the coupling characteristics or measurement detection.

The invention, additional features and advantages are explained more fully in the following with reference to the schematic drawings.

BRIEF DESCRIPTION OF THE DRAWINGS

FIG. 7 and 7a show the out-couple beam path with interference analysis;

FIG. 11 shows a variant of the beam guiding arrangement with absorption analysis.

DESCRIPTION OF THE PREFERRED EMBODIMENTS

Figure 1:
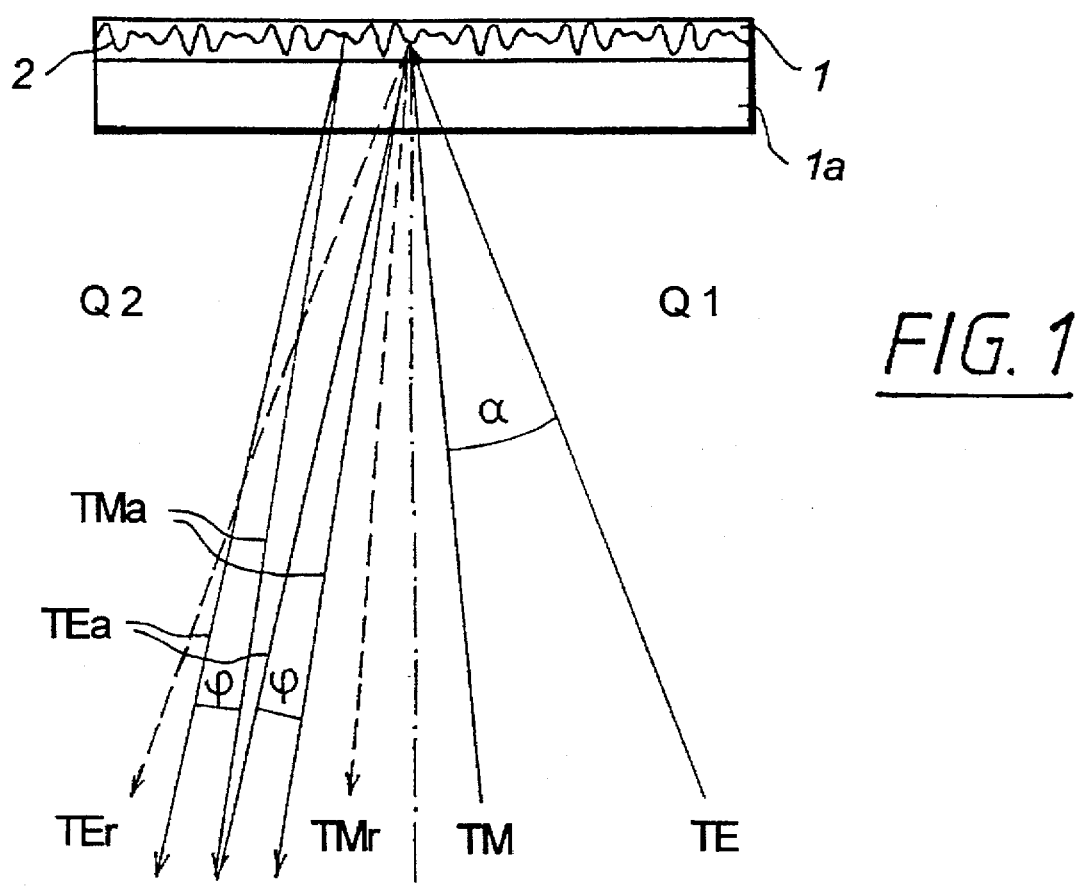
FIG. 1 shows a film waveguide as a component of an optical sensor with in-coupled, out-coupled and reflected beam components.

FIG. 1 is a schematic view of a film waveguide 1 on a substrate 1a which supports a bidiffraction grating arrangement 2 in a known manner. Two coherent, orthogonally polarized beam bundles $T_e$, $T_m$ are coupled into the film waveguide 1, these beam bundles $T_e$, $T_m$ enclosing an angle $\alpha$ and lying in a first quadrant $Q_1$ of the plane determined on the substrate side by incident and emergent beams.

The beams $T_{ea}$, $T_{ma}$ which are coupled out via the grating arrangement lie in quadrant $Q_2$ and enclose an angle $\phi$ which is appreciably less than angle $\alpha$. The out-coupled beams $T_{ea}$, $T_{ma}$ advantageously lie within an angular region formed by the reflected beam components $T_{mr}$, $T_{er}$ so that the reflected radiation components are separated from the out-coupled radiation components.

With interference analysis, angle $\phi$ is less than 6 degrees, preferably approximately 0.2–3 degrees, and angle $\alpha$ is greater than 6 degrees and is preferably in the range of 26 degrees plus/minus 20 degrees, more preferably 16 plus/minus 10 degrees.

At an angle $\alpha$ greater than 3 degrees, preferably 23 plus/minus 20 degrees or 13 plus/minus 10 degrees, $\phi$ is less than 3 degrees, preferably 0.2–3 degrees or 0.2–2 degrees.

When measuring by means of a position-sensitive detection system, $\alpha$ is greater than 2 degrees, preferably 22 plus/minus 20 degrees or 12 plus/minus 10 degrees, and $\phi$ is less than 20 degrees, preferably 0–12 degrees or 0–8 degrees.

Figure 2:
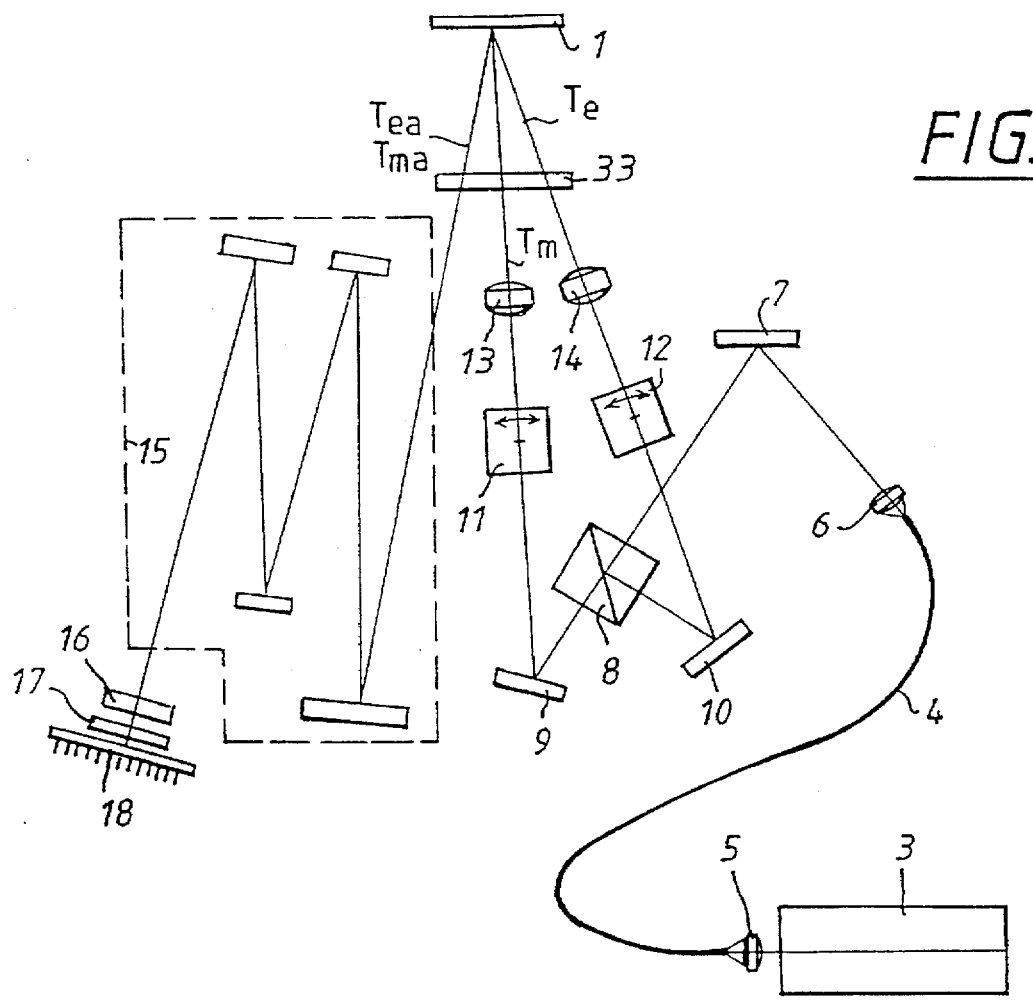
FIG. 2 shows the entire optical light path of the arrangement according to the invention.

FIG. 2 is an overall view of the arrangement according to the invention. The light from a laser light source 3 is coupled into a lightguide 4 via an in-coupling element 5 and strikes a first mirror 7 via an out-coupling and beam-shaping element 6 and then, proceeding from this first mirror 7, arrives at a polarizing beam splitter 8 which splits the light into two partial beam paths $T_e$ and $T_m$ which are coupled into the film waveguide via mirrors 9, 10, beam offsetting units 11, 12 and imaging systems 13, 14. An optical window 33 is provided between the sensor plane 1 and the rest of the arrangement to protect against external influences.

The sequence of focussing means 13, 14 and beam offsetting units 11, 12 is permutable. The lengths of the in-coupling paths for the two beam paths should be identical as far as possible, depending on the coherence length of the light source. Maximum differences of the optical paths for the two in-couple beam paths must be less than the coherence length of the light source in order to ensure the interference capability of the out-coupled modes.

The out-coupled beam modes $T_{ea}$ and $T_{ma}$ are imaged on a position-resolving receiver 18, e.g., a CCD array or diode array, via an imaging unit 15 which is shown in dashed lines and, as will be explained more fully with reference to FIG. 7, is formed, e.g., from a plurality of imaging mirrors, a polarizer 16 and an interference filter 17.

Figure 3:
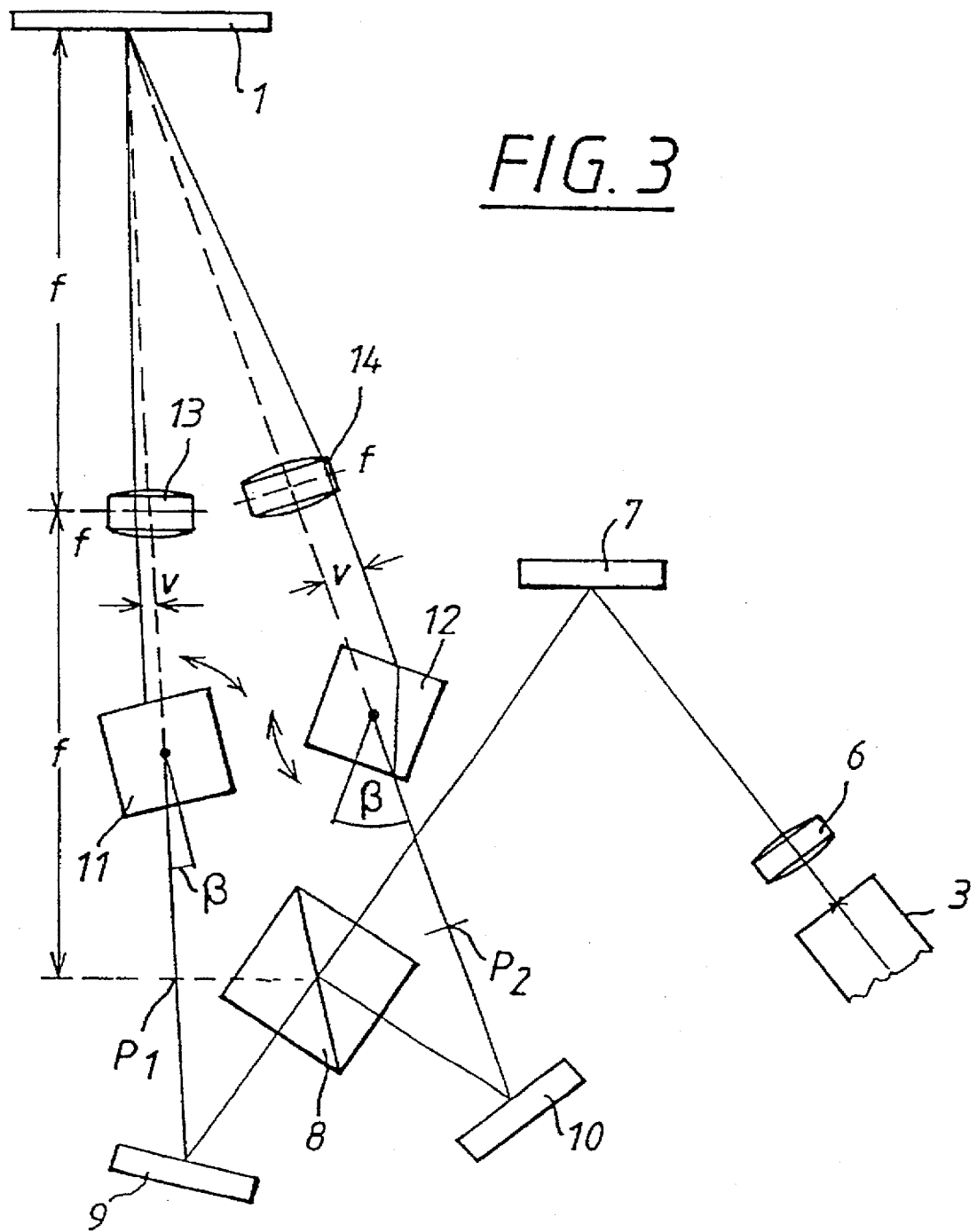
FIG. 3 shows the in-couple beam path.

The in-couple beam path is shown in an enlarged view in FIG. 3. The laser beam of the light source 3 is focussed by the out-coupling element 6 in such a way that the beam neck at points $P_1$, $P_2$ substantially corresponds to focal length f of the imaging lenses 13, 14.

The beam offsetting units 11, 12 are preferably swivelable plane-parallel glass parallelepipeds or plates and, depending on their rotational angle $\beta$, produce a beam offset V which causes a change in direction of the beam after passing through lenses 13, 14, wherein the in-coupling point in the sensor plane remains substantially stable.

In order to prevent disturbing reflections, it is advisable to incline the rotational axes slightly relative to the plane of incidence. In so doing, the in-coupled beam bundles have a slight convergence. Lenses 13, 14 are likewise arranged approximately at a distance f from the film waveguide.

The beam splitter 8 is preferably constructed as a semi-transparent mirror. However, beam splitting can also be effected via a beam splitter cube with a semitransparent coating, a holographic element or a glass-fiber branching element.

Integration (not shown) of beam deflecting 7 and beam splitting 8 in a polygon prism with reflecting surfaces, where appropriate, or in an integrated optical element is particularly advantageous.

Figure 4:
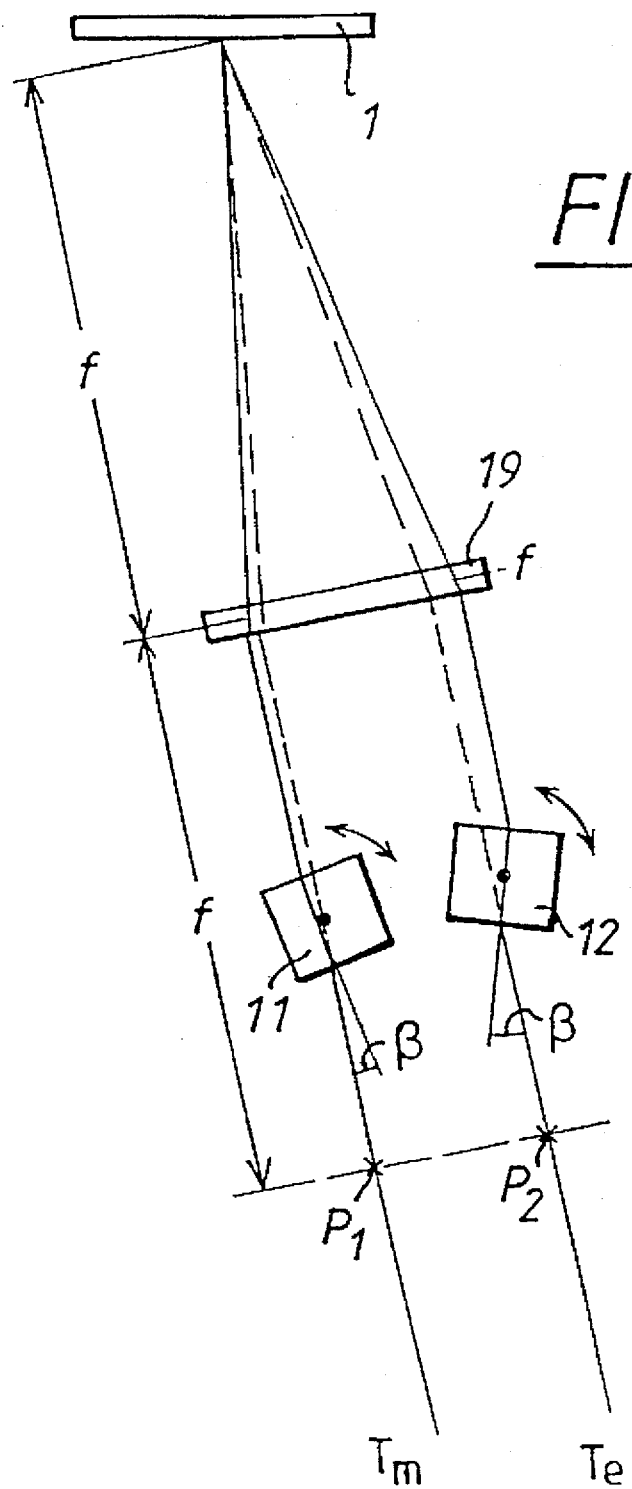
FIG. 4 shows another arrangement for in-coupling.

FIG. 4 shows an embodiment form as an alternative to FIG. 3 in which the two beam components $T_e$, $T_m$ are coupled in and changed with respect to their in-coupling angle in an analogous manner via a large lens 19. In so doing, it is necessary to guide the partial beams $T_e$, $T_m$ striking the elements 11, 12 substantially parallel to one another by means of suitable optical deflection (not shown).

Figure 5:
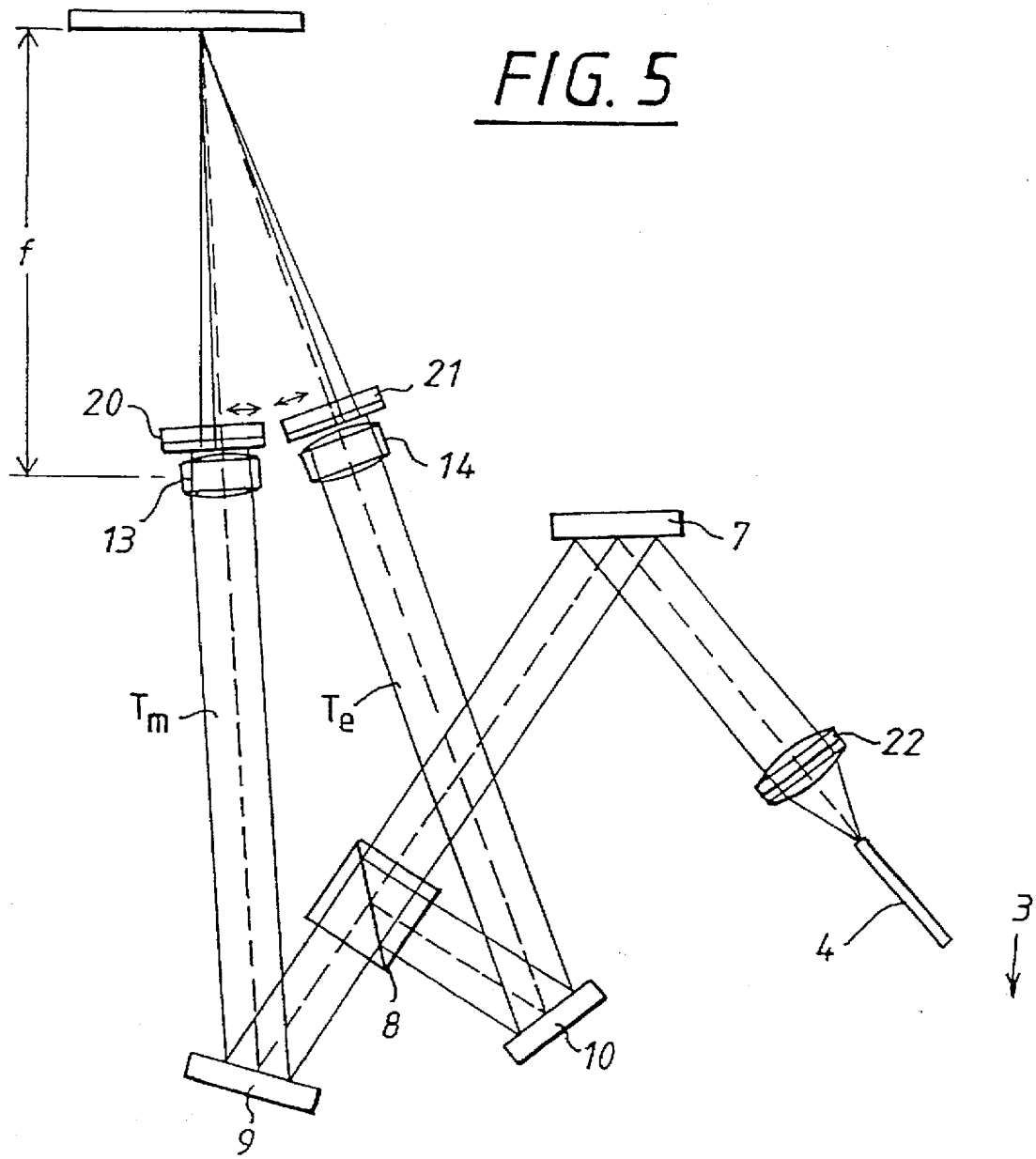
FIG. 5 shows a construction for angular adjustment of the in-couple beams.

FIG. 5 shows another method of angular displacement of the in-coupled beams. The beam bundles $T_e$, $T_m$ expanded by lenses 22 fully illuminate the cross section of the lenses 13, 14. Controllable slit diaphragms 20, 21 are arranged downstream of these lenses 13, 14 and only allow a partial beam bundle to pass, which partial beam bundle has an in-coupling angle which is changeable depending on the diaphragm position. These controllable slit diaphragms can be constructed mechanically and as LCD units or as diaphragms which are mechanically adjustable linearly or as filters with position-variable transmission characteristics.

The focussing value in the sensor plane is adjusted by changing the focal length of the lenses 13, 14 and/or the slit width or via a variable optical system. The focussing shape is influenced by the dimensions and shape of the slit. To compensate for the different focussing value in directions oriented vertically to one another, corrective optics, e.g., cylindrical optics, are included in the beam path upstream of the slit diaphragm or lenses 13, 14 are constructed in an appropriate manner.

A suitable beam shaping system for adapting the beam parameters which is formed of one or more imaging elements which can be constructed as reflective, refractive, holographic or Fresnel lenses can also be arranged downstream of the light source 3.

Figure 6:
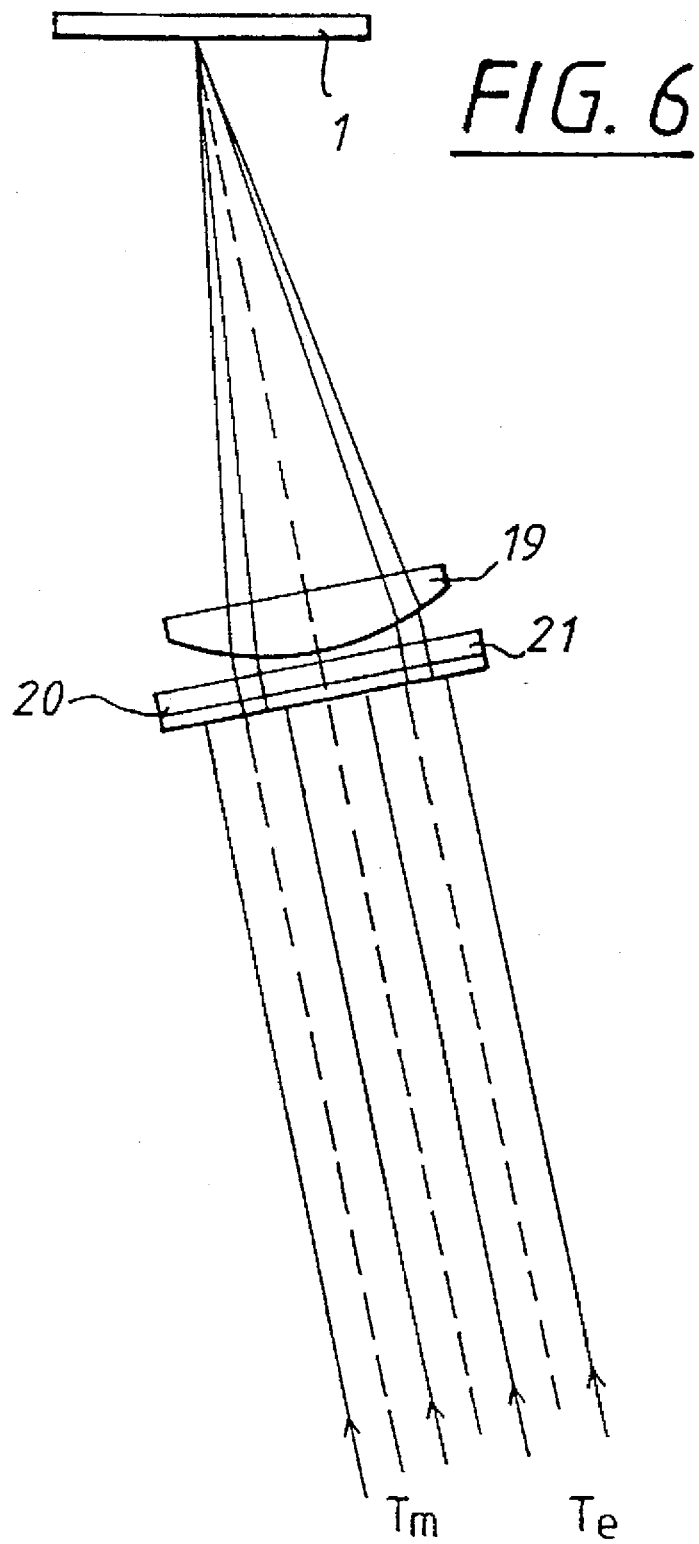
FIG. 6 shows another construction for angular adjustment.

In FIG. 6, the lenses 13, 14 according to FIG. 5 are replaced by a common lens 19, the diaphragms 20, 21 being provided in a combined arrangement, although they may be controlled separately. As in FIG. 4, substantially parallel partial beam bundles $T_e$, $T_m$ are generated by suitable optical means and pass through lens 19.

FIG. 7 shows an enlarged view of the out-coupled beam components $T_{ea}$ and $T_{ma}$ shown in FIG. 2 imaged on a position-resolving receiver 18. The change in the spatial interference pattern of $T_e$ and $T_m$ modes is recorded and evaluated as a measurement quantity in a known manner.

The interference pattern of the out-coupled beam components occurring at the point of exit is projected on the line receiver via cylindrical mirrors 23, 24 and spherical mirrors 25, 26 as an imaging magnified in the drawing plane. The cylindrical mirrors simultaneously cause a reduction in the interference pattern vertically to the drawing plane and accordingly adapt to the detector geometry in an optimal manner.

The optical imaging on the receiver array can also be realized by a lens system or by a combination of refractive imaging optics and reflective imaging optics. The refractive elements can be constructed as holographic elements or Fresnel lenses which can have different imaging characteristics in different directions. The line geometry can be adapted to in this way.

A polarizing filter 16 which causes the interference of the out-coupled modes required for the measuring process is to be arranged upstream of the detector 18. Further, a filter 17 with spectral selectivity can be arranged upstream of the detector for suppressing extraneous light. A window 33, preferably a plate with anti-reflection coating on both sides, can be arranged between the sensor plane and all optical components in order to protect against environmental influences.

The overall dimensions of the arrangement can be reduced and the receiver can be protected from unwanted influence of radiation by the folded beam paths within the imaging units.

The distance between the interference lines is determined from the interference pattern on the array as a measurement of the differential angle between the out-coupled beam components $T_{ea}$, $T_{ma}$, which is influenced in turn by the analysis substance on the film waveguide 1 and by its refractive index.

The overall dimensions of the arrangement can be reduced and the receiver can be protected from unwanted influence of radiation by the folded beam paths within the imaging unit.

High thermal stability of magnification is achieved for the imaging part 15 by constructing the optical element of fused quartz in combination with a mechanical support formed of material with adapted expansion coefficients, e.g., invar.

The imaging optical elements are held in the support block 31 which has drilled channels 32 for the optical beam paths. In order to compensate for thermal influences of the receiver 18 and the interference structure imaged on the array, a bushing 34 formed of a material with appropriately selected expansion coefficients is arranged between the support block 31 and the receiver 18. The expansion coefficient of the bushing 24 is determined from the difference in the expansion coefficients of the imaging elements and support block 31 and from the length ratio of the beam lengths extending in the support block 31 and in the bore holes. This is explained further with reference to FIG. 7a: Two structural component parts 34 and 35 of different material which are connected with one another only at points 36 and 37 are otherwise movable relative to one another. Due to the thermal expansion of the structural component parts 34 and 35 in opposite directions, it is possible to adjust a certain "effective" thermal expansion coefficient for the holder in its entirety by selecting the individual lengths and individual expansion coefficients. In this way, it is possible to compensate practically entirely for thermal drift between optical components and the housing relative to the detector.

Figure 8:
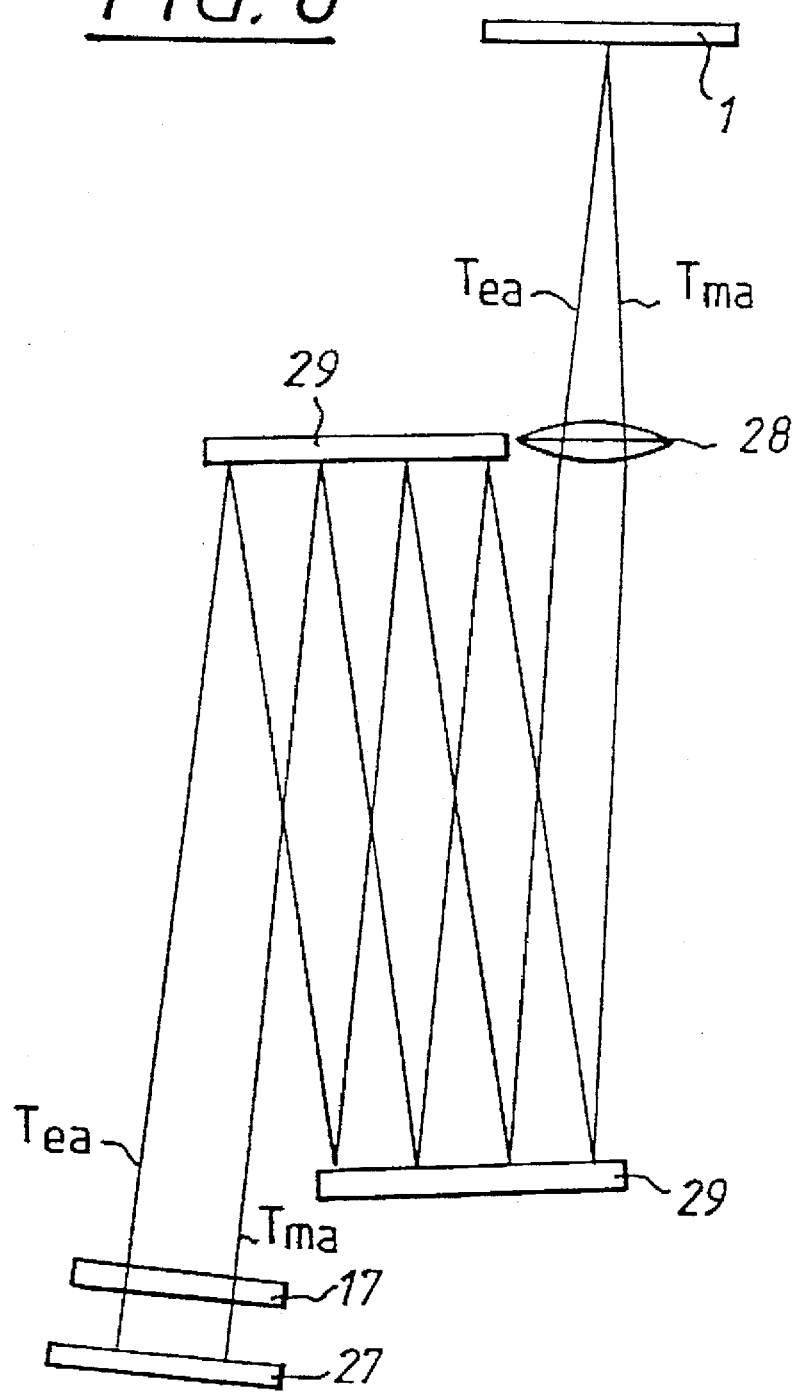
FIG. 8 shows the out-couple beam path with PSD analysis.

If the change in the differential angle $\phi$ of the out-coupled beam modes is not determined via the interference pattern, a position-sensitive detector 27 is provided as in FIG. 8, an image being formed on this position-sensitive detector 27 via a lens 28 and a mirror system 29. The detector 27 is at a distance from the lens 28 corresponding to the focal length. The angular difference is determined on the basis of the difference in position of the points of impingement.

The lens 28 can also be replaced by a plurality of lenses which can also be constructed as holographic elements or Fresnel lenses.

In an alternative arrangement of the out-couple beam path, a focus is produced in the detector plane for both out-coupled light fields. Changes in the distance between the two foci are utilized for analysis. For this purpose, a position-sensitive detector 27 is provided in FIG. 8, imaging being effected upon this detector 27 via a lens 28 and a mirror system 29. The detector 27 is arranged at a distance from lens 28 corresponding to the focal length.

In another possible out-couple beam path, the exiting light is focussed on a position-sensitive detector by a lens. In this embodiment form of the out-couple beam path of the TE mode and TM mode, a focus is produced in the detector plane in each instance and the in-couple beam paths are alternately switched by suitable optical means, e.g., shutters, in order to evaluate the distance between the two foci on the detector.

Further, the out-coupled light beams can be focussed on two position-sensitive detectors by a common lens or by two different lenses. A sufficient angular difference can be achieved in a simple manner when using a sensor with a bidiffraction grating coupler by selection of the grating constants. In this arrangement, the angles of the out-coupled TE and TM fields can be detected in parallel so that there is no need to switch the in-couple beams as was necessary in the embodiment form described above.

Figure 9:
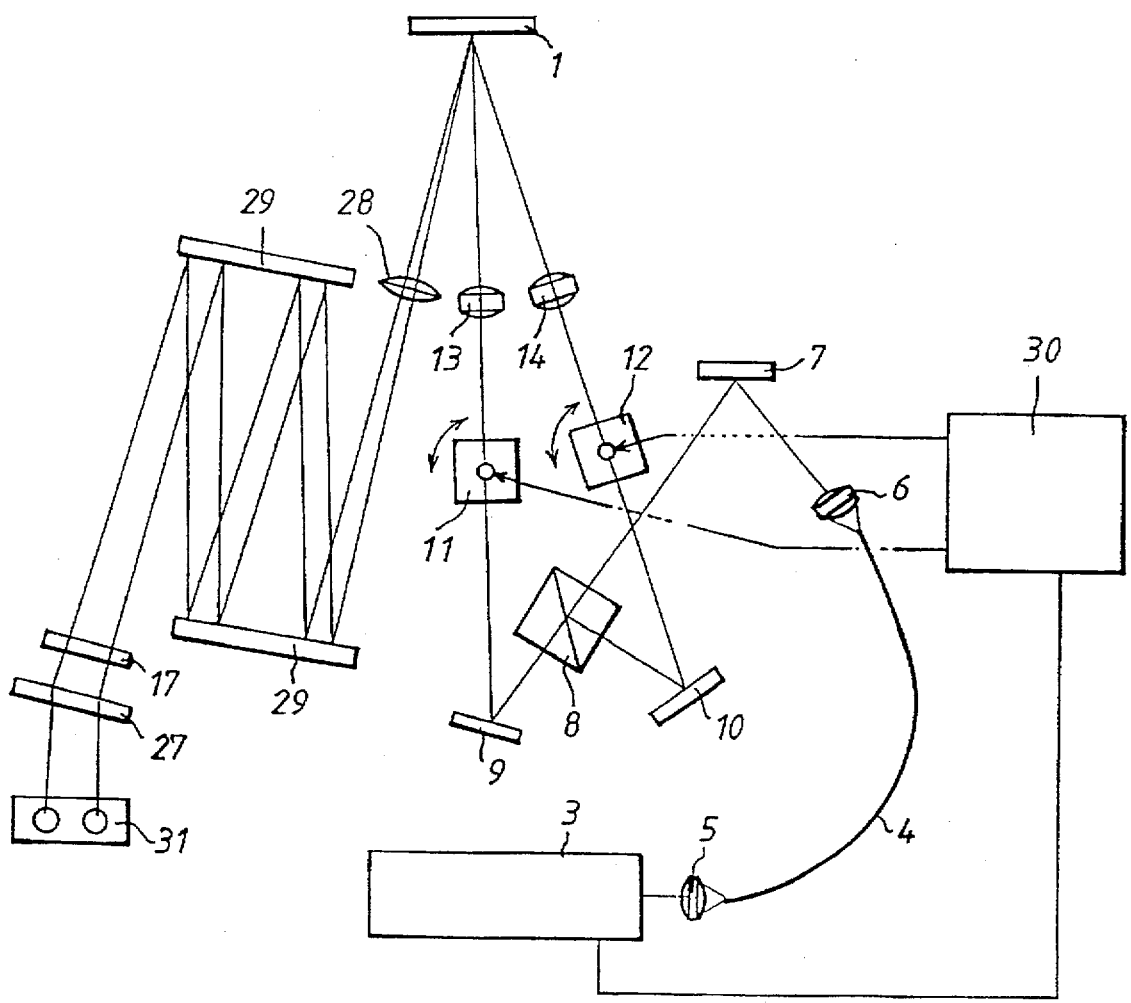
FIG. 9 shows in-coupling with rotatable beam offsetting units.

In FIG. 9, the beam offsetting elements 11, 12 are actuated in synchronous phase by means of a control unit 30. Images of the individual beam components appear on the receiver in temporal sequence at the times when the beam modes $T_e$ and $T_m$ are coupled. The signal difference on the PSD is a measurement for the differential angle of the out-coupled beams.

High thermal stability of magnification is achieved for the imaging part 15 by constructing the optical element of fused quartz in combination with a mechanical support formed of material with adapted expansion coefficients, e.g., invar.

Alternative combinations of materials with adapted thermal expansion coefficients for optical elements/optical supports are, e.g., zero-expansion glass ceramics (Zerodur, crown glass/gray cast iron, borosilicate glass (BK7, UBK7), crown glass/ceramics, crown glass/high-grade steel, crown glass/brass.

Figure 10:
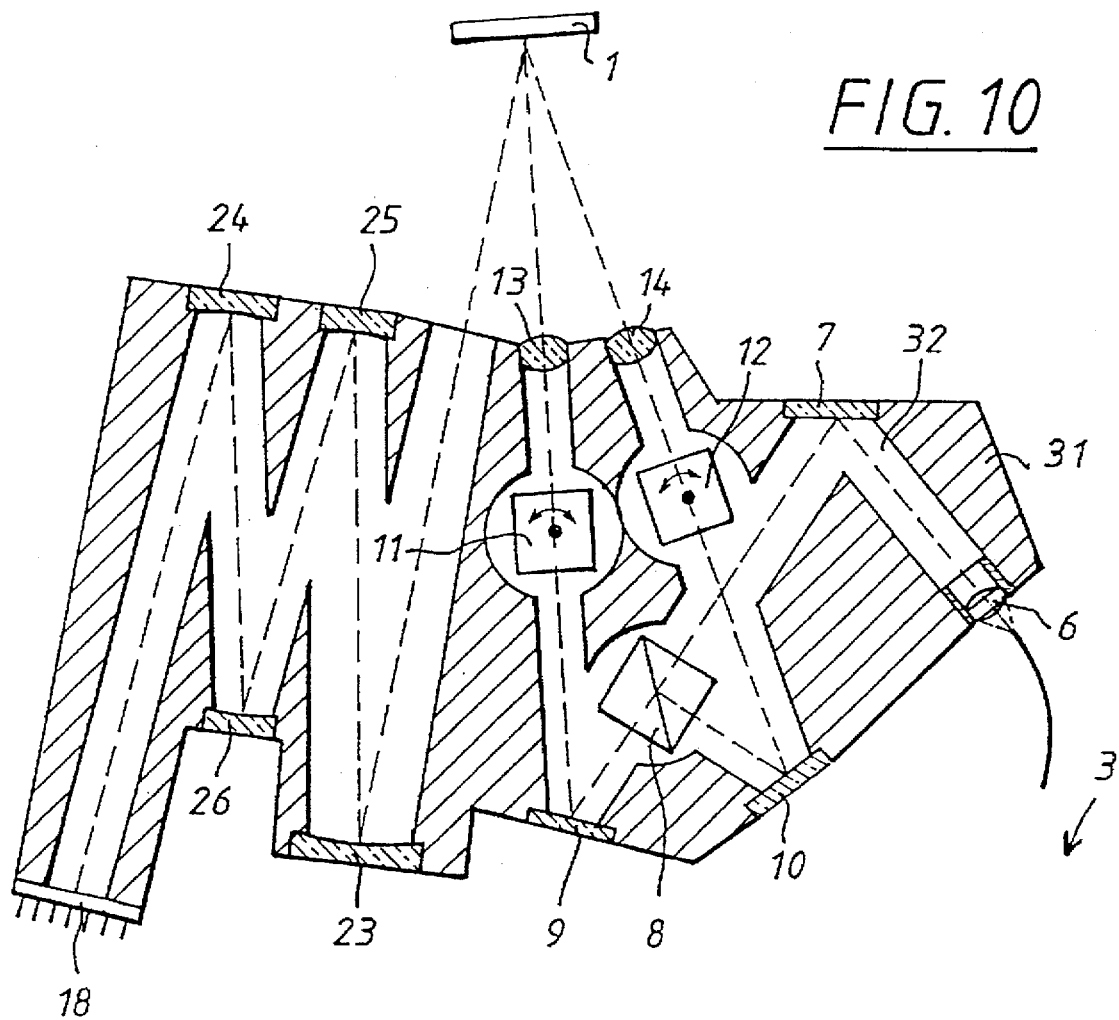
FIG. 10 shows a common support for the optical arrangement.

FIG. 10 shows the arrangement of the optical elements and beam paths in a common support block 31, shown in section, which has drilled channels 32 for the optical beam paths. The optical elements according to FIG. 2 are arranged, preferably cemented, externally at a common support block 31. Bore holes 32 are provided for the optical beam paths. An extremely stable arrangement, particularly with respect to occurring microphonics, is achieved by the defined relative position of the optical components. Optimal thermal stability of the arrangement can be realized by the selection of materials for the optical elements (e.g., glass, fused quartz) and for the support block (e.g., Zerodur, invar and gray cast iron) based on the thermal expansion coefficients. Reference is made to the preceding statements pertaining to selection of materials.

An arrangement with an in-coupled beam which is suitable for absorption measurement is shown in FIG. 11.

While the foregoing description and drawings represent the preferred embodiments of the present invention, it will be obvious to those skilled in the art that various changes and modifications may be made therein without departing from the true spirit and scope of the present invention.

List of References

[1] K. Tiefenthaler, W. Lukosz, "Integrated Optical Switches and Gas Sensors", *Optics Letters* 10, 137 (1984)
[2] T. Suhara, H. Nishihara, IEEE *J. Quantum Electron.* 22 845 (1986)
[3] W. Lukosz, K. Tiefenthaler: Patent EP 0226604
[4] W. Lukosz: Patent WO 8907756
[5] K. Tiefenthaler, W. Lukosz, "Sensitivity of grating couplers as integrated-optical chemical sensors", *J. Opt. Soc. Am.* B6, 209 (1989)
[6] K. Tiefenthaler: Patent EP 89108567
[7] W. Lukosz, Ph. M. Nellen, Ch. Stamm, P. Weiss, "Output Grating Couplers on Planar Waveguides as Integrated Optical Chemical Sensors", *Sensors and Actuators* B1, 585 (1990)
[8] Ph. M. Nellen, W. Lukosz, "Integrated Optical Input Grating Couplers as Chemo- and Immunosensors", *Sensors and Actuators* B1, 592 (1990)
[9] D. S. Goldmann, P. L. White, N. C. Anheier, "Miniaturized spectrometer employing planar waveguides and grating couplers for chemical analysis", *Applied Optics* 29, 4583 (1990)
[10] W. Lukosz, "Principles and sensitivities of integrated optical and surface plasmon sensors for direct affinity sensing and immunosensing", *Biosensors & Bioelectronics* 6, 215 (1991)
[11] Ch. Fattinger: Patent EP 0455067
[12] K. Tiefenthaler: Patent WO 9301487 EP 551456
[13] L. W. Burgess, Jr., D. S. Goldman: U.S. Pat. No. 5,082,629
[14] D. Clerc, W. Lukosz, "Integrated optical output grating coupler as refractometer and (bio-)chemical sensor", *Sensors and Actuators* B11, 461 (1993)
[15] Ch. Fattinger, "The bidiffracte grating coupler", *Appl. Phys. Lett.* 62, 1461 (1993)
[16] Ch. Fattinger: Patent Application CH 927/93

What is claimed is:

1. An arrangement for analysis of substances at or near the surface of an optical sensor, comprising:
    at least one wave-guiding film and at least one multidiffraction grating coupler for in-coupling and out-coupling of light beams;
    wherein at least two separate light beams enclosing an angle α relative to one another are coupled in and by which at least two light beams enclosing an angle φ relative to one another are coupled out;
    a detection system for detecting the out-coupled light beams; and
    wherein in-coupling and out-coupling are effected on one and the same side of the sensor and all the in-couple beams lie in a first quadrant of the plane of incident light and all the out-couple beams lie in a second quadrant of the plane of incident light, said first quadrant being different from said second quadrant, and the angle α between the in-couple beams is greater than the angle φ between the out-couple beams.

2. The arrangement according to claim 1, wherein the in-coupled light beams are polarized orthogonally relative to one another.

3. The arrangement according to claim 2, wherein the angular region of the out-couple beams lies within the angular region determined by the in-couple beams reflected at the sensor.

4. The arrangement according to claim 1, wherein the angular region of the out-couple beams lies within the angular region determined by the in-couple beams reflected at the sensor.

5. The arrangement according to claim 1, with the use of a position-resolving detection system, wherein an angle α of more than 6 degrees exists between the in-couple beams.

6. The arrangement according to claim 5, wherein an angle α between the in-couple beams lies in a range of approximately 26 degrees plus/minus 20 degrees.

7. The arrangement according to claim 5, wherein an angle φ between the out-coupled beams is than 6 degrees.

8. The arrangement according to claim 7, wherein an angle φ between the out-coupled beams lies in the range of approximately 0.2 to 3 degrees.

9. The arrangement according to claim 1, including means for independent adjustment of the in-couple angles of the in-coupled light bundles.

10. The arrangement according to claim 1, with the use of a position-resolving detection system, wherein an angle α of greater than 3 degrees lies between the in-couple beams.

11. The arrangement for analysis of substances according to claim 1, wherein the in-couple beams are adjustable with respect to their in-coupling angle and are also slightly convergent.

12. The arrangement according to claim 11, wherein the angles for the two in-couple beams are adjusted at the same time by a common element.

13. The arrangement according to claim 11, wherein the diameter of the in-couple beams in the sensor plane lies in the range of 10 µm to 1 mm.

14. The arrangement according to claim 1, wherein the optical arrangement for in-coupling and out-coupling is contained in a common housing.

15. The arrangement according to claim 14, wherein an arrangement of the light source outside a housing containing the rest of the measuring arrangement, wherein the light source is a laser or spectral lamp, and the light of the light source reaches the optical arrangement via a lightguide unit.

16. The arrangement according to claim 15, wherein a beam shaping system is arranged downstream of the light source for adapting the beam parameters, said beam shaping system having different characteristics parallel to and vertically to the plane of incidence.

17. The arrangement according to claim 16, wherein the beam shaping system is formed of holographic elements.

18. The arrangement according to claim 14, wherein components with adapted thermal expansion are used for optical elements and support elements for a temperature-stable image scale.

19. The arrangement according to claim 1, wherein components with adapted thermal expansion are used for optical elements and support elements for a temperature-stable image scale.

20. The arrangement according to claim 1, including means for photoelectric detection of the interference pattern generated by the overlapping of the out-coupled beams.

21. The arrangement according to claim 20, wherein the imaging of the interference pattern by at least one imaging element on a position-resolving detector which is connected with an evaluating unit.

22. The arrangement according to claim 21, wherein the position-resolving detector is a CCD element.

23. The arrangement according to claim 21, wherein the imaging element is at least one lens.

24. The arrangement according to claim 21, wherein the imaging element is at least one mirror.

25. The arrangement according to claim 1, wherein the out-coupled beam components are focussed on at least one receiver connected with an evaluating unit in order to determine the position and the angle φ of the out-coupled beams.

26. The arrangement according to claim 25, wherein the receiver is a PSD.

27. The arrangement according to claim 25, including an imaging beam path which is folded by means of mirrors.

28. The arrangement according to claim 25, including an alternating focussing out of the out-coupled radiation components on a position-resolving receiver.

29. The arrangement according to claim 28, wherein the in-coupling angles of the in-coupled beams are adjusted in phase synchronization relative to one another for time-offset out-coupling of the beam components.

30. The arrangement according to claim 1, wherein at least a portion of the optical elements are arranged in a common support block.

31. The arrangement according to claim 30, wherein the construction of at least a portion of the optical beam paths as bore holes is provided in the support block.

32. The arrangement according to claim 30, wherein a support block material is selected from the group consisting of invar, Zerodur or gray cast iron.

33. The arrangement according to claim 30, wherein the construction of a portion of the support block is made from a material whose thermal coefficient counteracts a thermal expansion of the rest of the support elements and/or the employed optics leading to measurement errors.

34. The arrangement according to claim 1, including means for using the angle conditions wherein an angle α of more than 6 degrees exists between the in-couple beams for the differential angle of in-coupling and out-coupling for absorption measurement.

35. The arrangement according to claim 1, including means for using the angle conditions wherein an angle α between the in-couple beams lies in a range of approximately 26 degrees plus/minus 20 degrees for the differential angle of in-coupling and out-coupling for absorption measurement.

36. The arrangement according to claim 1, including means for using the angle conditions wherein an angle φ between the out-coupled beams is less than 6 degrees for the differential angle of in-coupling and out-coupling for absorption measurement.

37. The arrangement according to claim 1, including means for using the angle conditions wherein an angle φ between the out-coupled beams lies in a range of approximately 0.2 to 3 degrees for the differential angle of in-coupling and out-coupling for absorption measurement.

38. The arrangement according to claim 1, including means for using the angle conditions wherein an angle of greater than 3 degrees lies between the in-couple beams for the differential angle of in-coupling and out-coupling for absorption measurement.

39. An arrangement for analysis of substances by measurement of light absorption at or near the surface of an optical sensor, comprising:

at least one wave-guiding film and at least one multidiffraction grating coupler for in-coupling and out-coupling of light beams;

wherein at least two separate light beams are coupled in and at least two light beams are coupled out, the in-couple beams lying at an in-coupling angle relative to one another;

a detection system for detecting the out-coupled light beams; and wherein in-coupling and out-coupling are effected on one and the same side of the sensor, all the in-couple beams lie in a first quadrant of the plane of incident light and all the out-couple beams lie in a second quadrant of the plane of incident light, said first quadrant being different from said second quadrant, and the in-couple beams are adjustable with respect to the in-coupling angle and are also slightly convergent.

40. The arrangement according to claim 39, including means for using said angle conditions for the differential angle of in-coupling and out-coupling for absorption measurement.

41. An arrangement for analysis of substances at or near the surface of an optical sensor, comprising:

at least one wave-guiding film and at least one multidiffraction grating coupler for in-coupling and out-coupling of light beams;

wherein at least two light beams enclosing an angle α relative to one another are coupled in, said at least two light beams lying in one and the same quadrant of the plane of incident light; and wherein the light from a light source reaches at least one beam splitter which splits it into at least two partial beams and the partial beams are guided into the sensor surface via beam-deflecting optics and beam offsetting units and at least one imaging unit.

42. The arrangement according to claim 41, wherein the radiated light is split into two orthogonally polarized partial beams.

43. The arrangement according to claim 41, wherein a polygon prism is provided for beam splitting and for beam deflection, and wherein at least one surface of the polygon prism is provided with a partially or fully reflecting coating.

44. The arrangement according to claim 41, wherein the incident light beams are focussed on the sensor plane.

45. The arrangement according to claim 44, wherein focussing is effected by imaging mirrors and/or by at least one lens.

46. The arrangement according to claim 45, wherein the lens or lenses for focussing on the sensor plane is/are constructed as holographic elements.

47. The arrangement according to claim 45, wherein the lens or lenses for focussing on the sensor plane is/are constructed as Fresnel lenses.

48. The arrangement according to claim 41, wherein the incident light beams are imaged by a first imaging unit in an intermediate focus in the vicinity of a beam offsetting unit and are focussed on the sensor surface by a second beam offsetting unit.

49. The arrangement according to claim 41, wherein the beam offsetting units are rotatable glass parallelepipeds.

50. The arrangement according to claim 41, wherein the beam offsetting units are rotatable mirrors.

51. The arrangement according to claim 41, wherein the beam offsetting units are controllable slit diaphragms which open only a portion of the beam path.

52. The arrangement according to claim 51, wherein the slit diaphragms are constructed as LCD units, linearly mechanically adjustable diaphragms, or linearly mechanically adjustable filters with position-variable transmission characteristics.

53. The arrangement according to claim 41, wherein beam splitting is effected by a glass-fiber branching element.

54. The arrangement according to claim 41, wherein at least a portion of the optical elements are arranged in a common support block.

55. An arrangement according to claim 20, including means for imaging an interference pattern of radiation components coupled out of a waveguide via the multidiffraction grating coupler, said means for imaging being formed of a combination of folded beam path and imaging mirrors arranged downstream of an exit location and operating to image the interference pattern on a position-resolving receiver via a polarizer.

56. The arrangement according to claim 55, including a telescopic imaging beam path.

* * * * *